United States Patent
Laor et al.

(10) Patent No.: US 9,693,747 B2
(45) Date of Patent: Jul. 4, 2017

(54) COMPUTED TOMOGRAPHY RADIATION DOSE CHECKER

(71) Applicant: Medic Vision Imaging Solutions Ltd., Tirat Carmel (IL)

(72) Inventors: Dan Laor, Haifa (IL); Eliran Dahan, Haifa (IL); Eyal Aharon, Kiryat Tivon (IL); Shai Attai, Shimshit (IL)

(73) Assignee: MEDIC VISION IMAGING SOLUTIONS LTD., Tirat Carmel (IL)

( * ) Notice: Subject to any disclaimer, the term of this patent is extended or adjusted under 35 U.S.C. 154(b) by 0 days.

(21) Appl. No.: 15/209,083

(22) Filed: Jul. 13, 2016

(65) Prior Publication Data

US 2017/0014095 A1 Jan. 19, 2017

Related U.S. Application Data

(60) Provisional application No. 62/192,605, filed on Jul. 15, 2015.

(51) Int. Cl.
*A61B 6/04* (2006.01)
*A61B 6/00* (2006.01)
*A61B 6/03* (2006.01)

(52) U.S. Cl.
CPC .............. *A61B 6/542* (2013.01); *A61B 6/032* (2013.01); *A61B 6/463* (2013.01)

(58) Field of Classification Search
CPC .. A61B 6/10; A61B 6/107; A61B 6/54; A61B 6/542; A61B 6/545; A61B 6/548; A61B 6/58; H05G 1/26; H05G 1/28; H05G 1/30; H05G 1/38; H05G 1/44; H05G 1/46; H05G 1/56
See application file for complete search history.

(56) References Cited

U.S. PATENT DOCUMENTS

| | | | | |
|---|---|---|---|---|
| 4,991,193 A * | 2/1991 | Cecil | ......................... | A61B 6/10 378/117 |
| 7,844,031 B2 * | 11/2010 | Newman | ............... | A61B 6/4233 378/114 |
| 8,085,901 B2 * | 12/2011 | Newman | ............... | A61B 6/4233 378/114 |
| 8,687,767 B2 * | 4/2014 | Newman | ............... | A61B 6/4233 378/102 |
| 8,690,425 B2 * | 4/2014 | Kopcienski | .......... | A61B 6/4405 378/102 |
| 9,295,146 B2 * | 3/2016 | Newman | ............... | A61B 6/4233 |
| 9,439,611 B2 * | 9/2016 | Peterson | .................. | A61B 6/40 |
| 2009/0129546 A1 * | 5/2009 | Newman | ............... | A61B 6/4233 378/114 |
| 2011/0096908 A1 * | 4/2011 | Newman | ............... | A61B 6/4233 378/116 |

(Continued)

*Primary Examiner* — Thomas R Artman

(74) *Attorney, Agent, or Firm* — Roy Gross; The Roy Gross Law Firm, LLC

(57) ABSTRACT

Devices and methods for embedding a standard dose checker feature within existing CT systems by obtaining and analyzing information from the existing CT system, detecting a radiation parameter value therefrom, comparing the detected radiation parameter with a predetermined threshold, and generating an operation-signal to affect the operation of the CT system based on the comparison between the detected radiation parameter and the predetermined threshold and the state of the CT system.

12 Claims, 11 Drawing Sheets

(56) References Cited

U.S. PATENT DOCUMENTS

| | | | |
|---|---|---|---|
| 2011/0123001 A1* | 5/2011 | Kopcienski | A61B 6/4405 378/198 |
| 2012/0093295 A1* | 4/2012 | Newman | A61B 6/4233 378/114 |
| 2013/0070896 A1* | 3/2013 | Newman | A61B 6/4233 378/62 |
| 2016/0038113 A1* | 2/2016 | Fan | A61B 6/037 378/19 |
| 2016/0278725 A1* | 9/2016 | Van Nijnatten | A61B 6/481 |
| 2017/0014095 A1* | 1/2017 | Laor | A61B 6/542 |

* cited by examiner

COMPUTED TOMOGRAPHY RADIATION DOSE CHECKER

TECHNICAL FIELD

The present disclosure generally relates to the field of Computed Tomography (CT) systems and uses thereof.

BACKGROUND

During CT scanning, target areas are subject to ionizing radiation to obtain multiple X-Ray images that are then computer-processed to be combined and produce cross-sectional topographic images of the target areas in the body of the subject. The dose of the ionizing radiation in CT is typically hundreds of times higher than the dose used in conventional X-ray imaging. It is well known that high dose of ionizing radiation can be harmful to the body.

To mitigate the risk or undesired high dose exposure to ionizing radiation, regulatory entities impose certain limitations and requirements on the operation of CT scanning machines. One example of these limitations and requirements exists in a standard named XR-29, which, among other requirements, requires embedding a "dose check feature" in the CT systems to prevent operating the CT machine at a dose higher than a determined threshold, unless explicit waver/permission is provided.

This requirement is being embedded in new CT systems, while older CT systems are left without it, and, therefore, do not meet the XR-29 Standard requirements.

There is thus a need in the art for devices and methods for embedding the "dose check feature" in existing CT systems not equipped with the manufacturer's embedded Dose Check feature.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

CT systems are quite expensive medical equipment, and their cost ranges from $ 200K to over $500K. Consequently, many medical care centers and providers of medical imaging services, which have already obtained a CT system, may not find it affordable to upgrade to new systems that meet the XR-29 Standard requirement.

According to some embodiments, there are provided herein devices, systems and methods for implementing/embedding the "dose check feature" in existing CT systems (aftermarket). Advantageously, embedding the "dose check feature" within existing CT systems provides compliance with state of the art standards without requiring medical care centers and providers of medical imaging services to purchase new CT systems.

According to some embodiments, a dose checker-device is introduced, including an input connector (input port) configured to be connected to a CT system in a non-intrusive manner, for example, through a video link within the CT system, a processing circuitry configured to detect a radiation parameter in the CT system, and a control unit configured to affect the operation of the CT system based on the detected radiation parameter.

The terms "dose checker device", "checker-device", "checker device", "checker", "CT checker" and "SafeCT-29", as used herein, are interchangeable.

The term "video link" as used herein refers to any link capable of transmitting imagery information to processors, monitors or other display devices.

According to some embodiment, there is provided a Computed Tomography (CT) checker device, comprising:
an input port configured to be associated with a CT-system, obtain scanning data and provide corresponding signal;
a processing circuitry, configured to:
obtain the scanning data from the input port;
detect a radiation parameter value from the scanning data;
compare the detected radiation parameter value with a predetermined threshold; and
generate an operation-signal based on the comparison, and
a control unit, configured to obtain the operation signal and affect an operation of the CT system based thereon.

According to some embodiment, the input port is configured to be associated with a display interface in the CT-system, wherein the scanning data is display imagery and wherein the signal is an internal-display signal, such that, the processing circuitry is configured to:
obtain the internal-display-signal from the input port;
analyze imagery depicted by the internal-display-signal;
detect the radiation parameter value from the analyzed imagery;
compare the detected radiation parameter value with a predetermined threshold; and
generate the operation-signal based on said comparison.

According to some embodiment, the terms "internal-display-signal" and "internal display signal" are interchangeable and may refer to an image, a screenshot and/or data representing an image.

According to some embodiments, the input port may be a video splitter. According to some embodiments, the input port may be a camera.

According to some embodiments, the radiation parameter includes a radiation dose.

The terms "established threshold" and "predetermined threshold" as used herein are interchangeable and refer to a radiation dose threshold. According to some embodiments, the threshold is based on an established, pre-defined, reference radiation dose level(s).

According to some embodiments, said control unit is configured to be connected to a control switch within the CT system and affect an operation of the CT system by toggling the state of the control switch thereby preventing radiation based on the comparison between the detected radiation parameter value and the predetermined threshold.

According to some embodiments, said affecting the operation comprises prevents initiation of scanning.

It is to be understood, that the device does not affect the CT system during operation, i.e., when scanning is performed. In contrast, the device includes safety means, such as, Interlock Override switch, that prevents its operation during scan acquisition.

According to some embodiments, the device further comprises a monitor, and said processing circuitry is further configured to provide a display signal to said monitor to indicate a state of operation of the device.

According to some embodiments, the state of operation of the device includes the detected radiation parameter value. According to some embodiments, the state of operation of the device includes a result of the comparison between the detected radiation parameter value and the predetermined threshold.

According to some embodiments, said processing circuitry is configured to provide a warning imagery to said display based on the comparison between the detected radiation parameter value and the predetermined threshold.

According to some embodiments, said device further comprises an output port configured to provide a display imagery signal to a monitor in the CT system, wherein the device is configured to be connected on the display link of the CT system and either pass an uninterrupted imagery from the input port to the output port, or provide an interrupted imagery from the input port to the output port based on the comparison between the detected radiation parameter value and the predetermined threshold.

According to some embodiments, said device further comprises an interface configured to obtain control-input from a user and affect the operation of the device accordingly.

According to some embodiments, said device is configured to operate a multi-level check, in which the radiation parameter is compared with a plurality of thresholds.

According to some embodiments, said detecting a radiation parameter value from the analyzed imagery comprises performing an optical character recognition on the analyzed imagery.

According to some embodiments, there is provided a method for CT dose optimization and management, the method comprising:
  obtaining an internal signal from a CT system;
  detecting a radiation parameter value from the internal signal;
  comparing the detected radiation parameter value with a predetermined threshold; and
  generating an operation-signal based on the comparison between the detected radiation parameter value and the predetermined threshold,
wherein the operation-signal is configured to affect an operation of the CT system.

According to some embodiments, the internal signal from the CT system is an internal-display-signal, wherein said method further comprises analyzing imagery depicted by the internal-display-signal, such that the radiation parameter value is detected from the analyzed imagery.

According to some embodiments, the method further comprises monitoring the operation of the CT system, and preventing the operation-signal from affecting an operation of the CT system if the CT system is in the midst of scanning.

According to some embodiments, said detecting the radiation parameter value from the analyzed imagery comprises performing an optical character recognition on the analyzed imagery.

According to some embodiments, said detecting a radiation parameter value from the analyzed imagery comprises identifying a term referring to the radiation parameter, and detecting a numerical value associated with the identified term.

According to some embodiments, the method further comprises toggling a control switch within the CT system based on the operation-signal.

According to some embodiments, said toggling a control switch comprises preventing initiation of scanning at the CT system.

According to some embodiments, said CT system is having a door switch loop configured for preventing initiation of scanning at the CT system and said control switch is connected to the door switch loop.

According to some embodiments, said control switch is configured to prevent interruption of the CT operation if CT scanning is being performed.

According to some embodiments, said control switch may be overridden to prevent interruption of the CT operation in case of a failure in the Dose checker device.

According to some embodiments, there is provided a method for CT dose optimization and management, the method comprising:
  providing a CT checker device, comprising
    an input port, configured to be associated with a CT-system, obtain scanning data therefrom, and provide an internal signal;
    a processing circuitry, configured to:
      obtain the internal signal from the input port;
      detect a radiation parameter value from the internal signal;
      compare the detected radiation parameter value with a predetermined threshold; and
      generate an operation-signal based on the comparison, and
    a control unit, configured to obtain the operation signal and affect an operation of the CT system based thereon,
  obtaining an internal signal from a CT system;
  detecting a radiation parameter value from the internal signal;
  comparing the detected radiation parameter value with a predetermined threshold; and
  generating an operation-signal based on the comparison between the detected radiation parameter value and the predetermined threshold,
wherein the operation-signal is configured to affect an operation of the CT system.

According to some embodiments, said input port is configured to be connected to a display interface in a CT-system, said scanning data is display imagery and said internal signal is an internal-display-signal.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
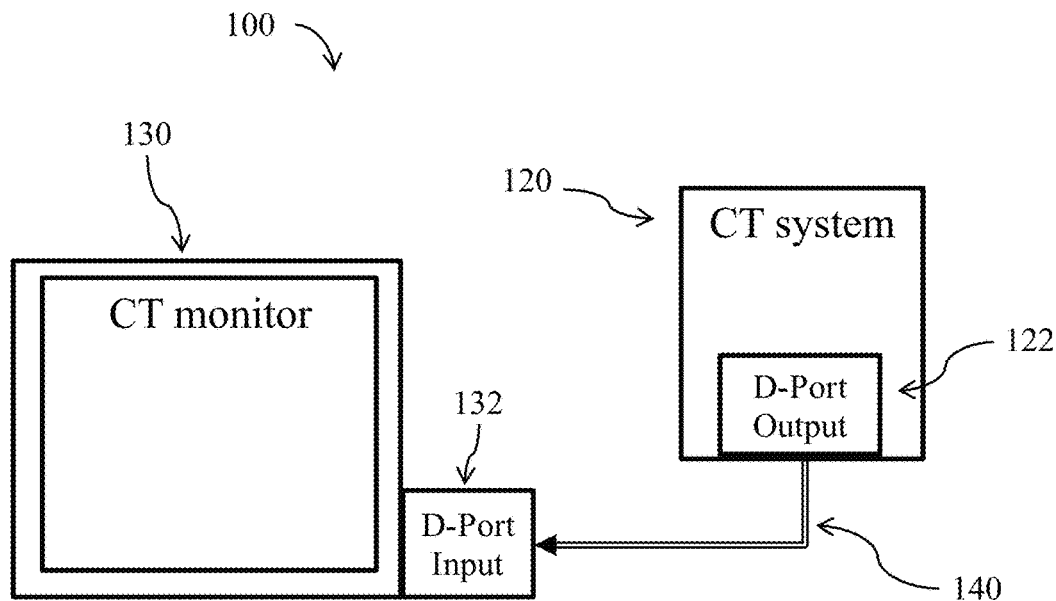
FIG. 1 schematically illustrates a common CT system to monitor connectivity.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there are provided herein devices, systems and methods for implementing the "dose check feature" in existing commercial CT systems. Advantageously, embedding the "dose check feature" within existing CT systems provide numerous advantages, including, but not limited to:

(i) provides compliance with state of the art standards without requiring medical care centers to purchase new CT systems and supports specified legally marketed CT scanners of any vendor presenting estimated dose on the CT operator's display prior to the scan;

(ii) designed to operate in the various display protocols of any scanner and any CT scanner software versions, which display the dose information in different formats and locations on the CT console display;

(iii) includes a configuration file, which defined the various scanners known in the art and their corresponding software versions, together with the related information on the location of the relevant information on the CT display and the scanner's workflow. The configuration file is updated occasionally, such that the relevant details of every new CT scanner model that is introduced to the market are added thereto. An exemplary list of scanners and the corresponding Software (SW) versions included in a given configuration file is provided in Table 1.

TABLE 1

An exemplary configuration file

| Manufacturer | CT Model | SW/OS Version |
| --- | --- | --- |
| GE | Discovery LightSpeed | OS SUN OS 5.8 |
| GE | Discovery RX | dm09__dvctsp1.23 |
| GE | Discovery ST | dm09__hl2sp1.23 |
| GE | LightSpeed Plus | 308-2__H3.1M5 |
| GE | LightSpeed Pro 16 | 07MW11.10 |
| GE | LightSpeed VCT | gmp__vct.42 |
| Philips | Brilliance 64 | 3.5.5 |
| Philips | Brilliance 64 | 2.6.2 |
| Philips | GeminiGXL 16 | 2.2.5 |
| Toshiba | Acquilion | V3.35ER007 |

(iv) does not alter the integrity of the CT system, thus, post implementation of the dose check feature all the functions of the CT scanner are preserved. Moreover, dose check feature implementation does not affect the design nor operation of the scanner (i.e. none of the CT controls such as X-ray, motion, GUI are affected). This advantage is conferred by the fact that the entire dose check feature system, including the software, is separated from the CT scanner. In fact, the dose check feature software runs on an independent computer and no 3rd party software runs on the CT Console (or any other part of the scanner);

(v) interfaces with the CT system through standard connections;

(vi) continuously receives the CT Console display video: the CT protocol and radiation dose information (calculated by the scanner) that are displayed to the CT operator may be extracted and analyzed in real time by the checker-device software. To this end, the checker-device software may include certain measures aimed to ensure correct reading of the data items. Thus, the checker-device presents dose notifications and prevents over-dose scanning in a timely manner, that is, it does not cause delays in operating the CT scanner. According to some embodiment, the checker-device performs its required functionality within less than 300 ms, i.e. from the time a certain data item (e.g. dose level) appears on the screen until the required action is performed (e.g. display a notification message). According to some embodiment, the checker-device software includes a watchdog mechanism in order to protect from software or hardware failures that may cause the system to stop responding.

According to some embodiments, a checker-device is introduced, including an input connector, configured to be associated with a CT system, a processing circuitry configured to detect a radiation parameter in the CT system, and a control unit configured to affect the operation of the CT system based on the detected radiation parameter.

According to some embodiments, the input connector (also termed 'input port') is a remote input connector, and is not physically linked to the CT system.

According to some embodiments, the input port is connected to the CT system.

According to some embodiments, the radiation parameter includes a radiation dose.

According to some embodiment, the radiation dose is expressed in terms of $CTDI_{vol}$, optionally, in units of milliGrays or in CT power distribution unit (CT PDU).

According to some embodiments, the radiation parameter includes radiation intensity. According to some embodiments, the radiation parameter includes radiation frequency.

According to some embodiments, the radiation parameter includes radiation amplitude at various frequencies. According to some embodiments the radiation parameter includes radiation duration. According to some embodiments, the radiation parameter includes any combination of the above.

According to some embodiments, the radiation parameters are compared to an established threshold (predetermined threshold or predefined threshold).

According to some embodiments, the radiation parameters are compared to a plurality of thresholds. According to some embodiments, the processing circuitry configured and/or control unit are configured to affect the operation of the CT system based on the comparison between the radiation parameter(s) and the thresholds.

According to some embodiments, affecting the operation may include presenting a warning message. According to some embodiments, affecting the operation may include sounding and/or producing an alarm. According to some embodiments, affecting the operation may include obstructing radiation. According to some embodiments, affecting the operation may include switching a safety switch (toggle).

Figure 12:
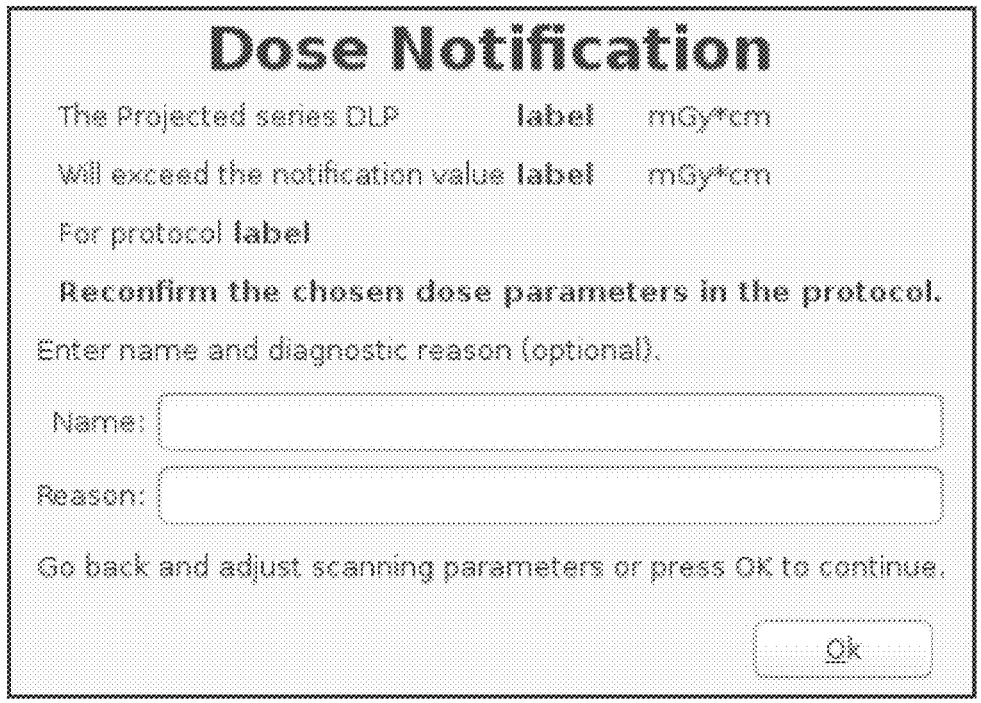
FIG. 12 illustrates an exemplary dose notification, according to some embodiments.
Figure 13:
FIG. 13 illustrates an exemplary dose alert, according to some embodiments.

The terms "warning message", "warning imagery", "alarm", "alarm message" and "alarm imagery", as used herein, are interchangeable and may refer to a message as exemplified in FIGS. 12 and 13.

Figure 4:
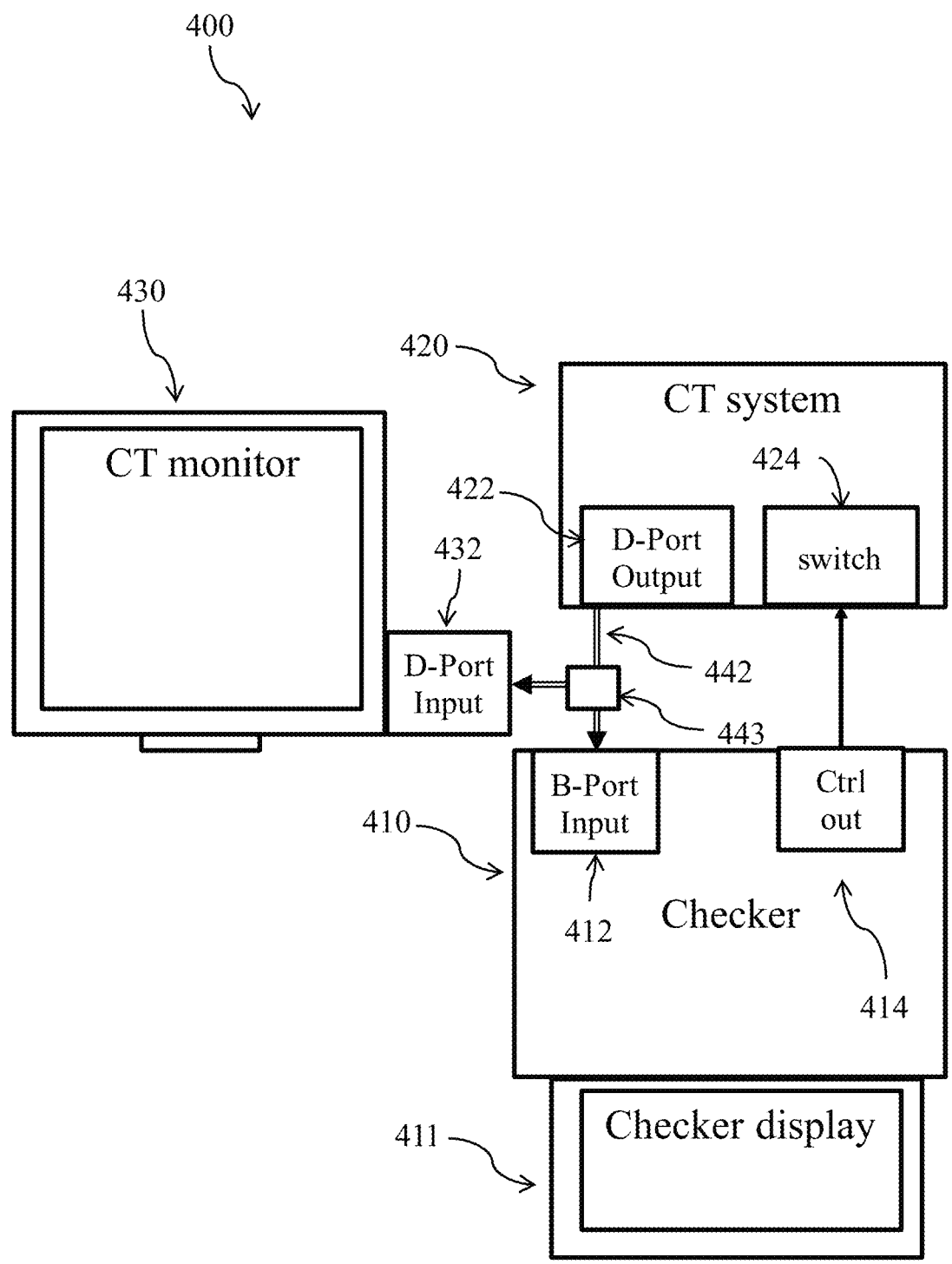
FIG. 4 schematically illustrates a system with a CT checker not intervening with the CT monitor link, according to some embodiments.

The terms "control switch", "safety switch" and "toggle", as used herein, are interchangeable and may refer to a switch as exemplified in FIG. 4.

According to some embodiments, checker-device interfaces with the CT system through standard connections in accordance with the CT manufacturer recommendations.

According to some embodiments, checker-device interfaces with the CT system through a connection selected from the group consisting of: (1) the CT Console video output, (ii) the CT door Switch loop, and (iii) the X-ray warning light circuit.

Reference is now made to FIG. 1, which schematically illustrates a common setting 100 of a CT system 120 to CT monitor 130 connectivity. According to some embodiments, CT system 120 is commonly connected to CT monitor 130 by a display link 140 connected to an output display port 122 in CT system 120 and an input display port 132 in CT monitor 130.

Display link 140 and display input and output ports 132 and 122 may include standard display connections such as Composite video, SCART, S-Video, CGA, MDA, HCG, EGA, Amiga video, VGA, GVIF, OpenLDI, DVI, SDI, HDMI, DisplayPort, DiiVA, HDBaseT, CoaXPress, MHL, or the like.

According to some embodiments, the CT checker is configured to obtain display signal(s) from the display link, analyze an image depicted by the signal(s), detect a radiation parameter, and compare the detected parameter with a predefined threshold or range of values. According to some embodiments, the device is further connected to a control switch to affect the operation of the CT system based on the comparison.

Figure 2:
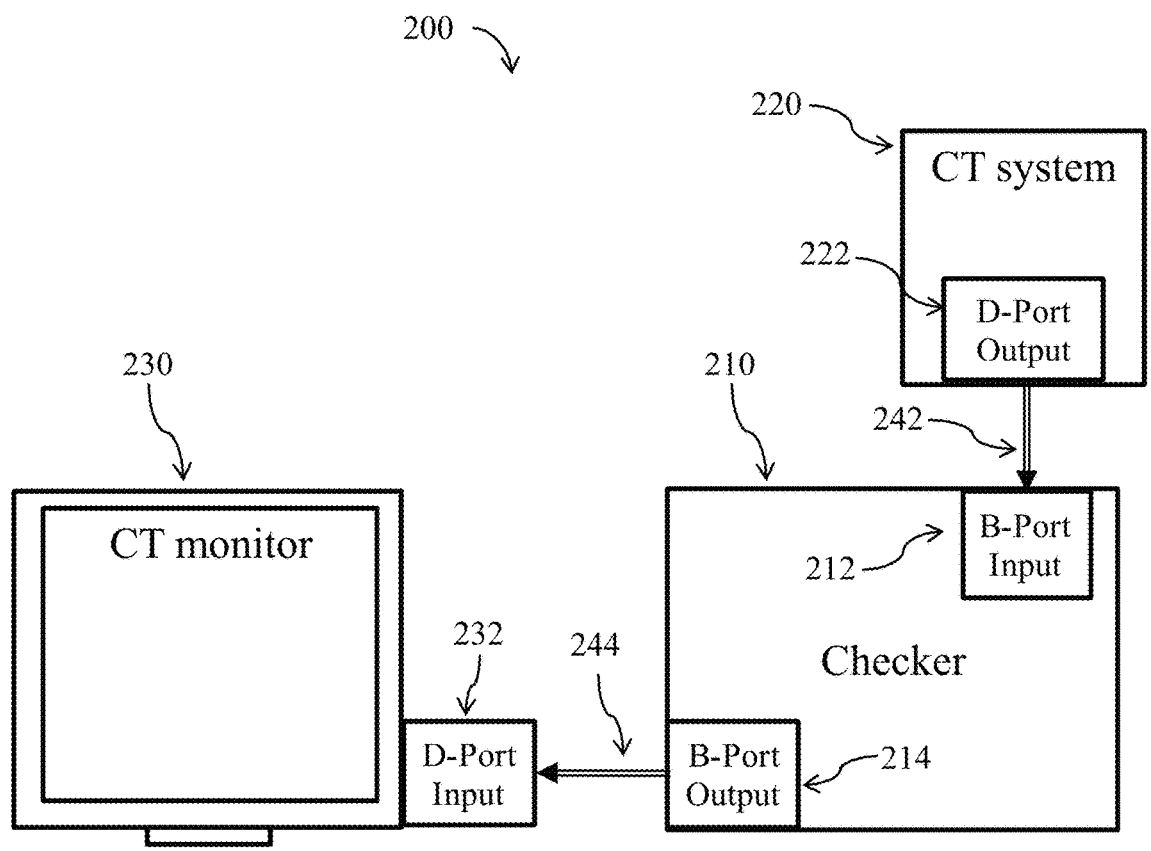
FIG. 2 schematically illustrates a system with a checker connected between the CT system and the CT monitor, according to some embodiments.

Reference is now made to FIG. 2, which schematically illustrates a setting 200 with a CT checker 210 connected between the CT system 220 and the CT monitor 230, according to some embodiments. According to some embodiments, CT system 220 generates display information and provides it through an output port 222 to a display link 242. CT checker 210 is connected to display link 242, and configured to analyze the imagery depicted therein to detect a value of a radiation parameter.

Then CT checker 210 either provides the same image uninterruptedly through a checker output display port 214 via a checker display link 244 to a monitor input port 232 to be displayed on CT monitor 230, or interferes with the image, for example by introducing warning messages, based on the value of the detected parameter.

Figure 3:
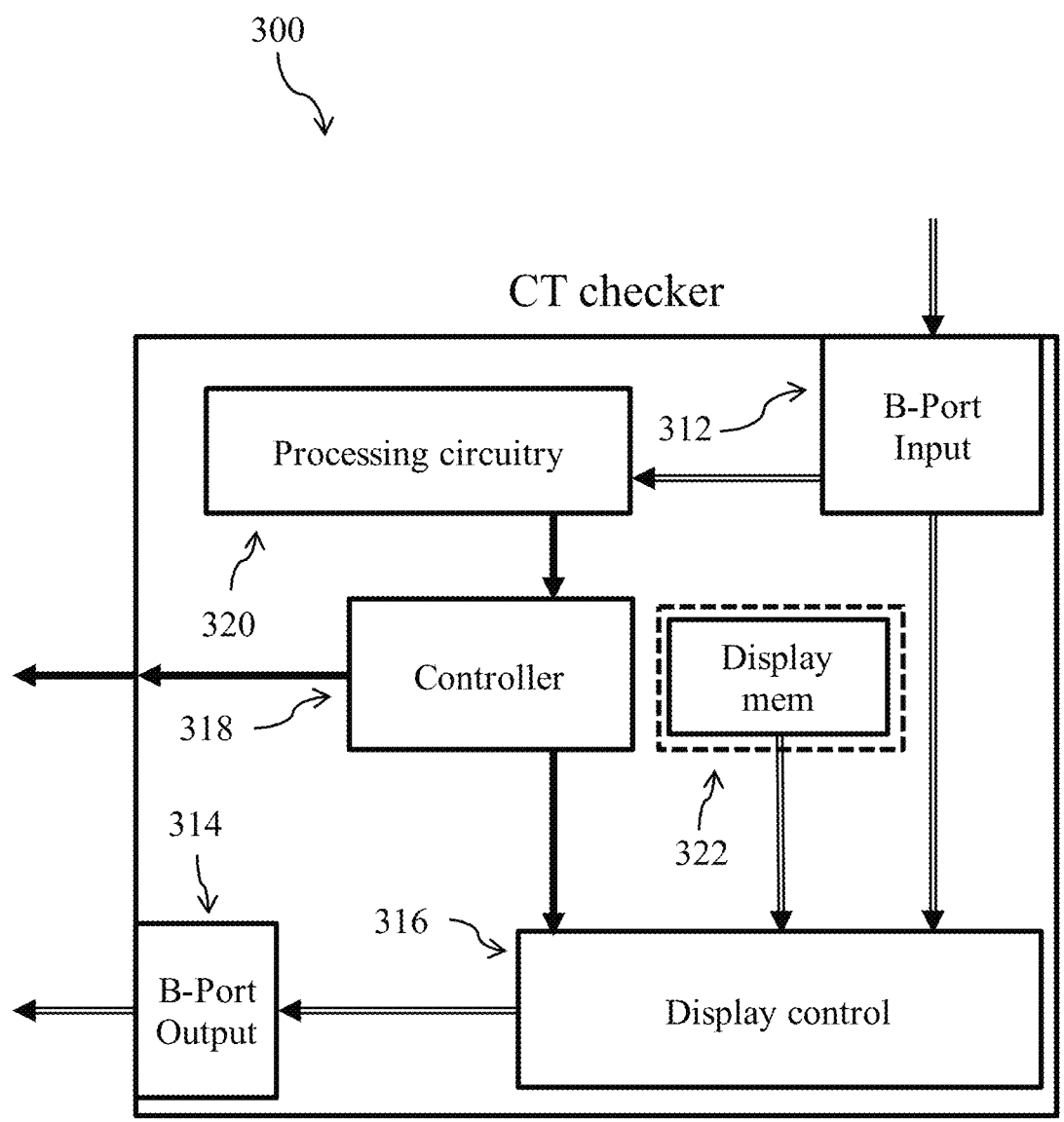
FIG. 3 schematically illustrates a CT checker with CT monitor control, according to some embodiments.

Reference is now made to FIG. 3, which schematically illustrates a CT checker 300 with CT monitor control, according to some embodiments. According to some embodiments, CT checker 300 includes a checker input display port 312 configured to obtain a display signal from a CT system, and provide the signal to a display controller 316 and a processing circuitry 320. According to some embodiments, processing circuitry 320 is configured to analyze the provided imagery, and detect a radiation parameter, then to compare it with a predetermined threshold value or range, and accordingly instruct a controller 318 to interfere with the operation of the CT system, and/or configure display controller 316 to affect a change on an image provided to a CT monitor through a checker output display port 314. According to some embodiments, CT checker 300 may further include a display memory 322 having stored thereon predefined imagery to be displayed as requested by controller 318.

According to some embodiments, the predefined imagery may be a warning signal and or a notification. According to some embodiments, the warning signal may include a warning text.

According to some embodiments, the CT checker is configured to be connected to the display link of the CT system, without interrupting the signal provided to the CT monitor.

Reference is now made to FIG. 4, which schematically illustrates a setting 400 with a CT checker 410 not intervening with a CT monitor link 442, according to some embodiments. According to some embodiments, CT checker 410 is configured to obtain a display signal through a checker input display port 412, the signal depicting imagery data provided by a CT system 420 through an output display port 422 therein, to a CT monitor 430 through an input display port 432 therein.

According to some embodiments, CT checker 410 is configured to analyze the imagery, detect a parameter value therefrom, and compare the value with a predefined threshold or range, and, based on the comparison criteria, provide a control signal to CT system 420 via a control output 414, for example, to control an operation safety switch 424 in CT system 420.

According to some embodiments, said safety switch 424 is the door switch loop of the CT system.

According to some embodiments, CT Checker 410 may further include a checker display 411 configured to display information related to the checker comparison status, detected parameter, and the like.

According to some embodiments, setting 400 includes a video splitter 443, configured to obtain the video signal from CT system 420 and split it to be provided to CT 360 monitor 430 and checker 410.

According to some embodiments, the Video splitter is configured to capture images from the CT monitor (CT Operator display video) and sends a copy of same video/image signal to a Video Grabber. This function may be performed continuously and automatically (such that the video splitter can be always "on" with no requirement for user action or interface). According to some embodiments, The Video Splitter is a passive device that takes the output signal out of the CT console and splits that into two identical output signals: one configured to be provided to the CT system (CT console) and the other goes to the checker (SafeCT-29 system).

According to some embodiments, a checker processing circuitry (SafeCT-29 Computer) may include an Off-The-Shelf (OTS), high quality video splitter that ensures that the quality of the image displayed on the CT console is maintained without significant or any image quality degradation.

According to some embodiments, technical characteristics of the SafeCT-29 Video Splitter may include: 2 Port Internal Video Splitter, Video Input: 15-pin HD-15 connector, Video Output: 2×15-pin, HD-15 connectors, Bandwidth of 250 MHz, Supported VGA Modes: All modes up to 1920×1440, Power: 5V 200 mA, Fault tolerant output port, Integrated ground loop isolation, Low voltage circuitry and OS Support: Linux.

Figure 5:
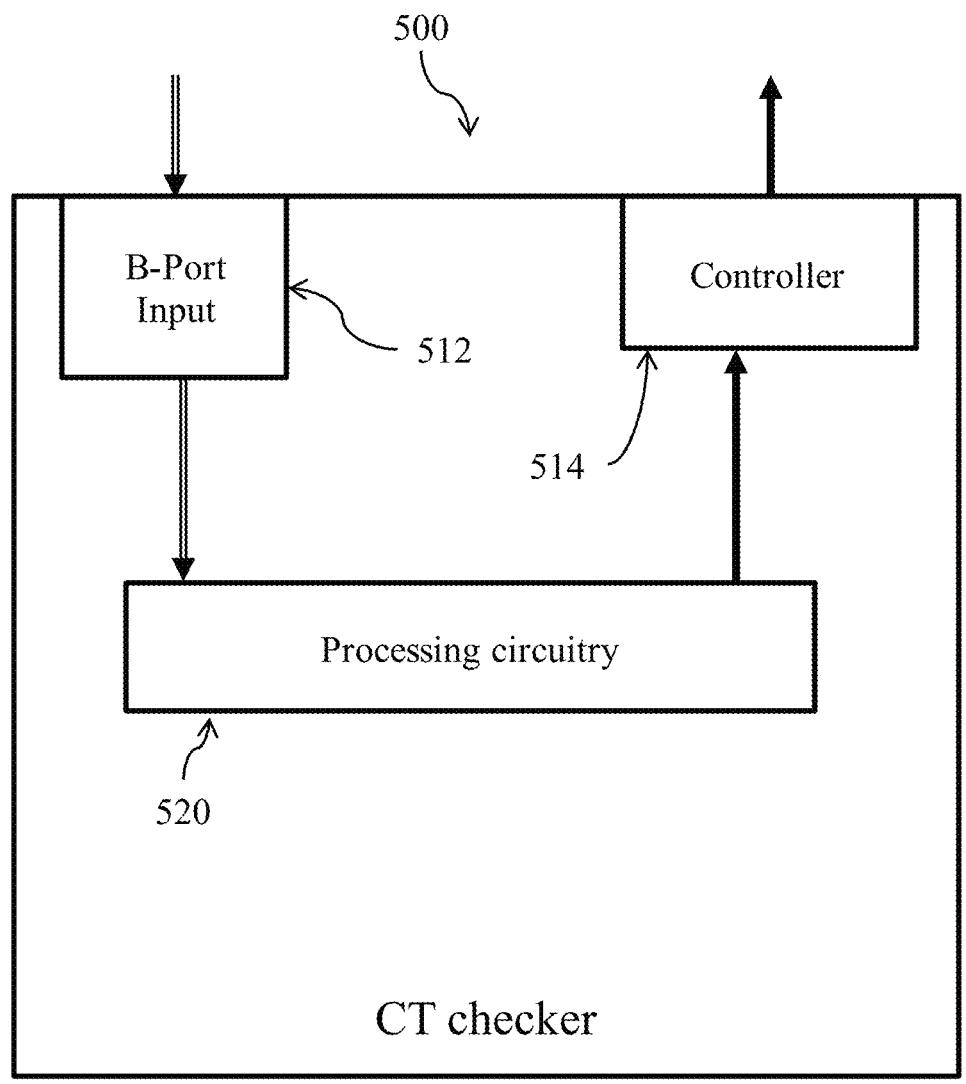
FIG. 5 schematically illustrates a CT checker without a CT monitor control, according to some embodiments.

Reference is now made to FIG. 5, which schematically illustrates a CT checker 500 without CT monitor control, according to some embodiments. According to some embodiments, CT checker 500 is configured to obtain a display signal through a checker input port 512, then analyze imagery depicted in the signal utilizing a processing circuitry 520 to detect a radiation parameter, and check the parameter using a defined criteria, and provide a control signal through a controller 514 based on the parameter value and the criteria.

Figure 6:
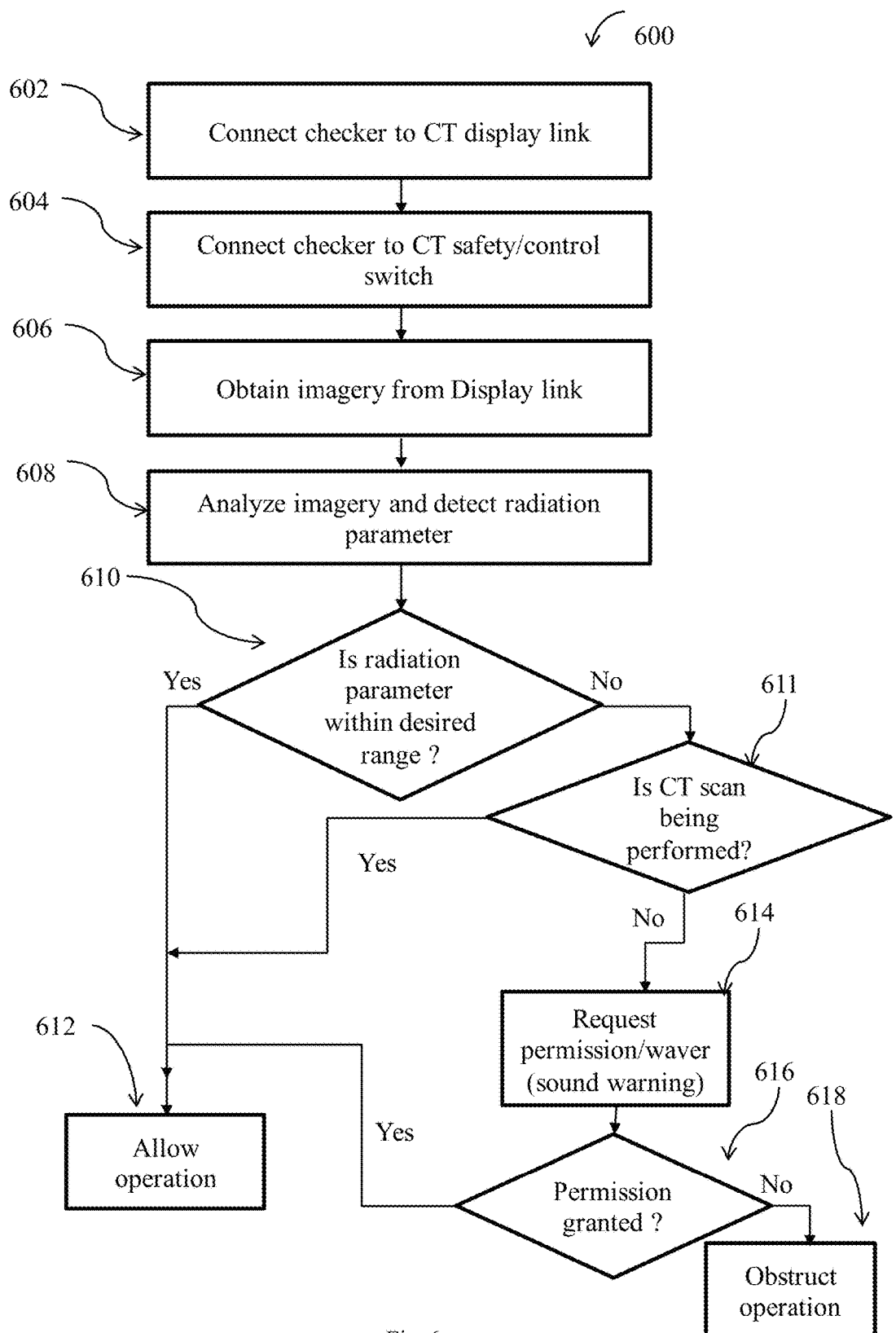
FIG. 6 illustrates a flow chart of a method of operating a checker, according to some embodiments.

Reference is now made to FIG. 6, which illustrates a flow chart of a method 600 of operating a checker, according to some embodiments. According to some embodiments, method 600 begins by connecting the checker to a CT display link (step 602), and connect the checker to a CT safety/control switch (step 604), then obtain imagery from the display link (step 606), and analyze the imagery to detect a radiation parameter (step 608). Then, the detected parameter is compared with a threshold or a defined criteria (step 610), and if the parameter passes the criteria, CT operation is allowed (step 612), otherwise, the state of the CT system is checked to verify if a scan is already being performed (step 611). If so, the checker allows the CT system to continue scanning with no interruption. Otherwise, a permission/waver is requested (step 614), and if the permission is granted (step 616) operation may be allowed (step 612), otherwise, operation will be obstructed (step 618).

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

EXAMPLES

Example 1. Video Splitter Connections

The Checker-device may include a Video Splitter aimed to prevent interference with the functionality of the CT system through the CT video connection (which may result in a poor display or absence display on the CT Operator's Display). The Video Splitter may exert its beneficial activities by operating as follows:

1. ensure no loss in picture quality, resolution or power and no additional loading limitations on the video cables.

2. has an integrated ground loop isolation circuitry eliminating all VGA noise caused by a ground loop.

3. is Fault-tolerant, providing a video output that is identical to the input even when the device fails or powered-off. The fault-tolerant output is connected to the CT Operator's display, thus ensuring proper operation of the scanner in case of checker-device failure.

4. uses a low voltage transition-minimized differential signaling circuitry to ensure that it cannot cause damage to the CT display or the video source (the CT Console).

5. when the checker-device software identifies noise, instability and/or artifacts in the video signal, or no signal, a warning message is displayed on the checker-device Display, to alert the CT Operator of such display noise.

Example 2. System Architecture and Components

Figure 7A:
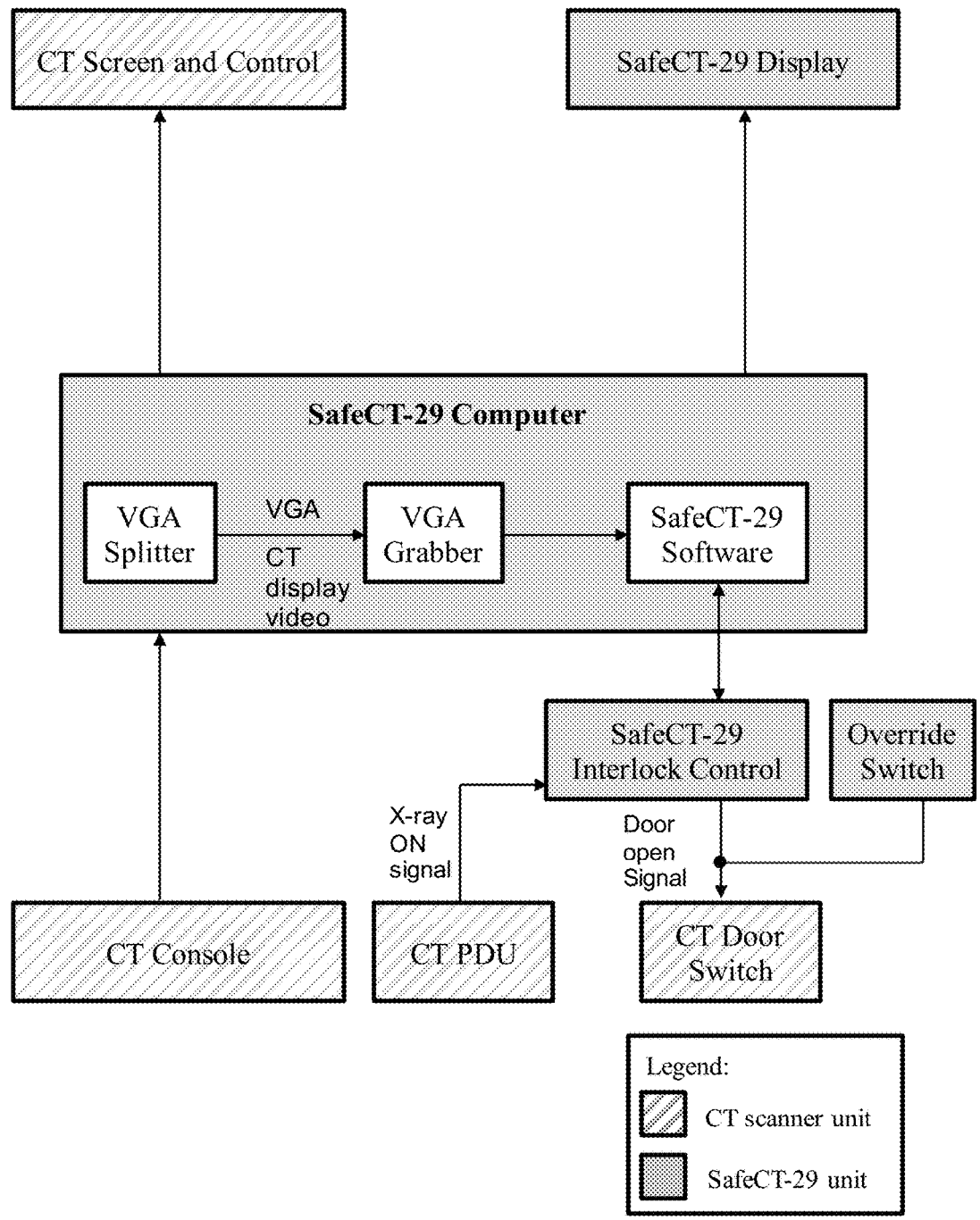
FIG. 7A schematically illustrates a setting with a SafeCT-29 checker, according to some embodiments.
Figure 7B:
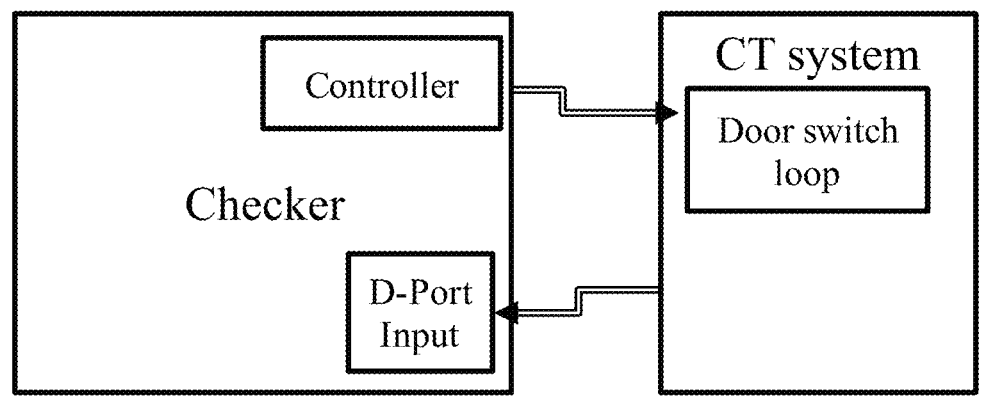
FIG. 7B schematically illustrates a setting with a SafeCT-29 checker, according to some embodiments.

An exemplary SafeCT-29 and its components and sub-systems is depicted in FIGS. 7A and 7B. The SafeCT-29 Computer may hosts a Video Splitter, a Video Grabber and the SafeCT-29 Software. The SafeCT-29 Computer may also manage the SafeCT-29 display and may control the SafeCT-29 Interlock Switch.

According to some embodiments, the Video splitter captures the CT Operator display video and sends a copy of same video signal to the Video Grabber. This function is performed continuously and automatically (the video splitter is always "on"; no user action or interface required). In fact, the Video Splitter is a passive device that takes the output signal out of the CT console and splits it into two identical output signals: one goes to the CT console and the other goes to the SafeCT-29 system.

According to some embodiments, the Video Grabber captures and converts an analog video signal, such as the signal produced by a CT Console to be displayed on the CT display, to digital video. The resulting digital data are computer files referred to as a video stream.

The SafeCT-29 Computer may include an OTS, high quality video grabber, which operates continuously and automatically (the video grabber is always "on"; no user action or interface required).

The rate of the grabber sampling is controlled by the SafeCT-29 software. When the software identifies that the CT is NOT in Scan or Preparation for scan mode, the sampling rate is lowered to prevent overheat and unnecessary power consumption.

The SafeCT-29 Display may be used to display the Dose Notification to the CT operator. It is a separate independent monitor (i.e., not the CT console display), that is "always on" (no "sleep mode").

Figure 8:
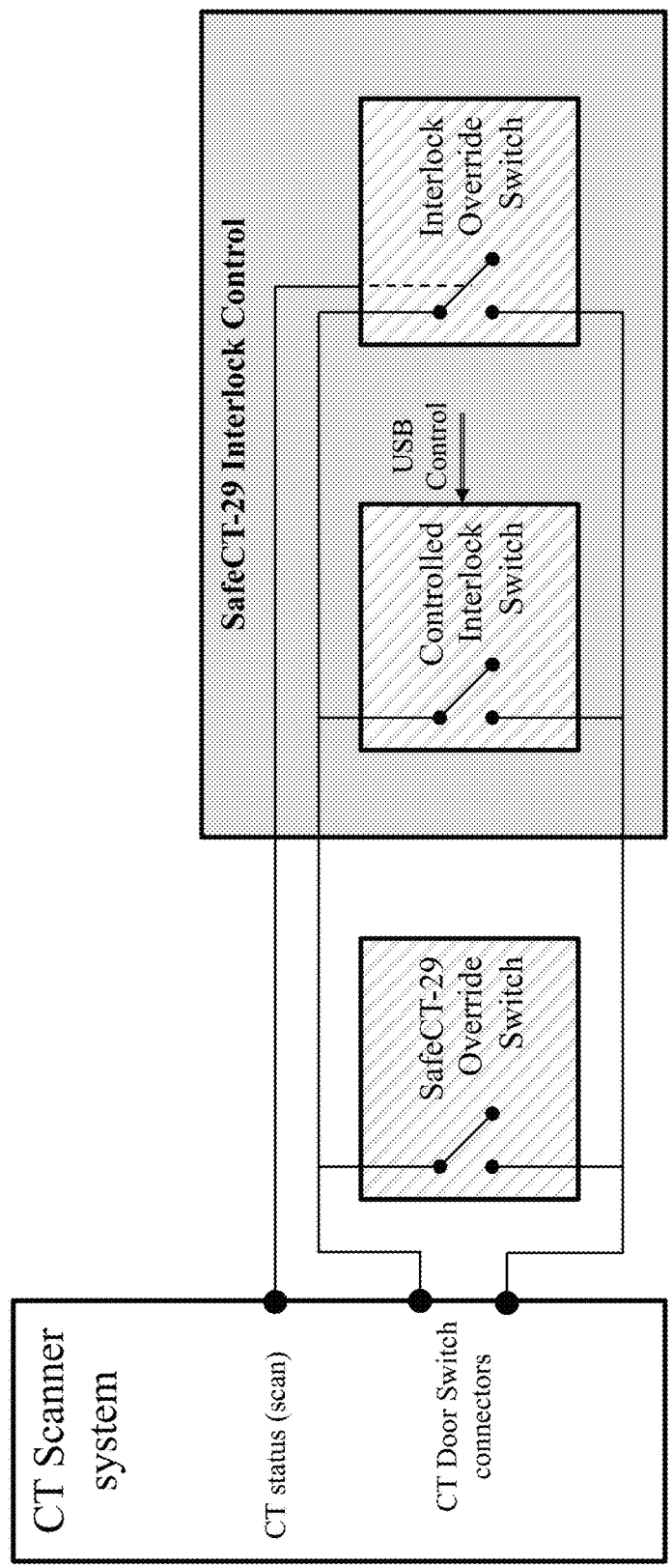
FIG. 8 schematically illustrates a setting with a SafeCT-29 checker, according to some embodiments.

According to some embodiments, the SafeCT-29 may further include an Interlock Control comprising two controlled relays: Controlled Interlock Switch and Interlock Override Switch (FIGS. 7A and 8). The control relays prevent over-the-limit scans while ensuring that the SafeCT-29 system does not interfere with the scanner during a scan, even in case of malfunction or failure. The SafeCT-29 monitors the Interlock Control status to ensure proper operation and alerts the user in case of a failure.

According to some embodiments, the SafeCT-29 Interlock Control is connected to the related CT output port, following the CT Manufacturers' instructions. In conformance to the requirements of the 21CFR subchapter J, all CT systems include output ports for connecting door switches (FIGS. 7A and 7B) and X-Ray On warning lights and the connection instructions.

According to some embodiments, the checker controller is connected to the door switch loop of the CT System (FIG. 7B).

According to some embodiments, when the estimated dose level exceeds the predetermined threshold, a Notification or Alert is displayed on the SafeCT-29 Display, and the SafeCT-29 Computer generates a signal that opens the Interlock switch, thus preventing the scan.

Figure 9:
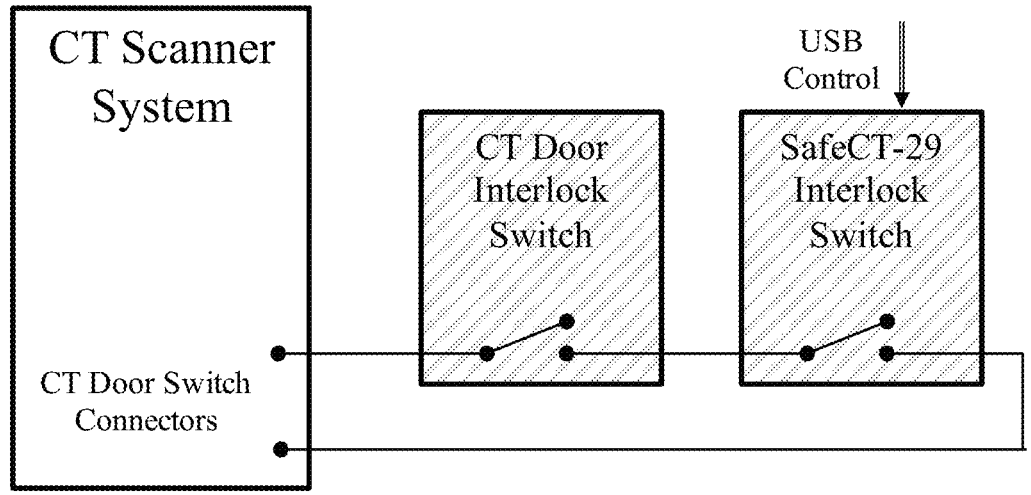
FIG. 9 schematically illustrates a setting with a SafeCT-29 checker, according to some embodiments.
Figure 10:
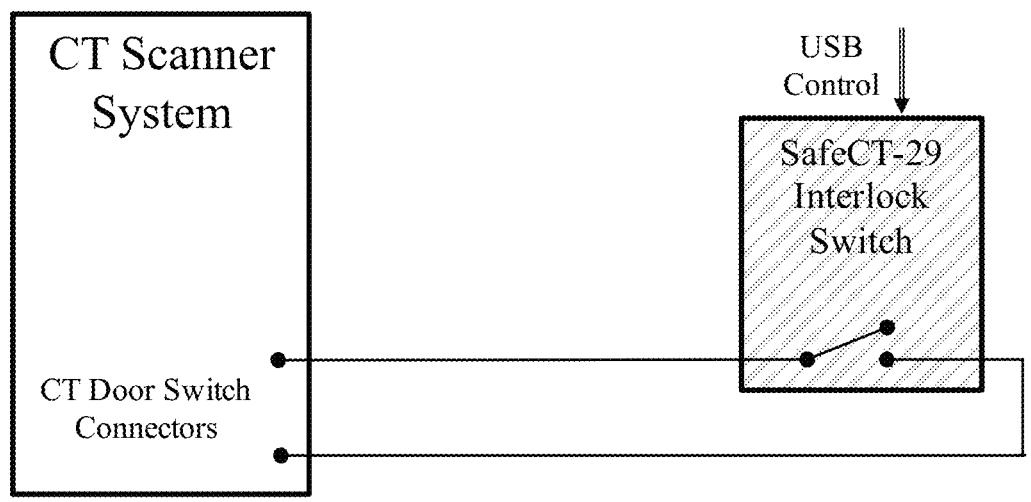
FIG. 10 schematically illustrates a setting with a SafeCT-29 checker, according to some embodiments.

The Controlled Interlock Switch is a relay configured to stop a device upon the occurrence of certain events. CT systems contain a "Door Switch" which includes an interlock switch that stops the CT scan (or prevents initiating a new scan) when the CT room door is open. The SafeCT-29 Controlled Interlock Switch, which is controlled by the SafeCT-29 software (e.g., via USB connector), may be connected in series with the CT Door interlock switch (FIG. 9). In case a CT Door Switch is not installed at the site, the SafeCT-29 Interlock Switch may be connected directly to the door switch connectors CT System (FIG. 10).

Upon system initialization, the SafeCT-29 Computer may generate a signal (e.g., via the USB link) that sets the Controlled Interlock Switch so that scans can be performed. The switch opens the door switch loop by the SafeCT-29 Computer, when a Notification or Alert is displayed, thus preventing the operator from scanning in over-dose, as defined in XR-25 Standard.

Figure 11:
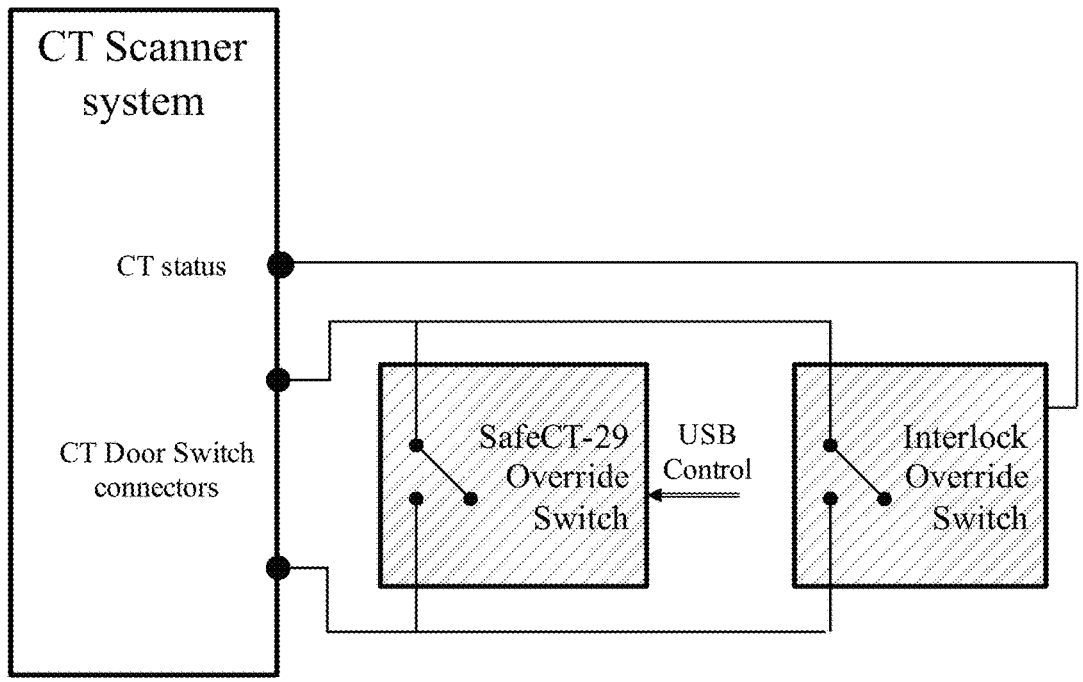
FIG. 11 schematically illustrates a setting with a SafeCT-29 checker, according to some embodiments.

The Interlock Override switch prevents a potential accidental interruption during a scan, by the SafeCT-29 system. The Interlock Override switch, may be connected in parallel to the Controlled Interlock Switch (FIG. 11), is controlled by the CT X-ray ON warning signal (which, controls the X-Ray On lights). Whenever the X-Ray-on light signal is active ("Light On"), the Interlock Override switch is closed, thus overriding the entire SafeCT-29 system and preventing any accidental interruption during a scan.

The Interlock Override switch may be interfaced to the CT PDU (CT power distribution unit) conforming to the CT manufacturer's X-Ray light instructions.

According to some embodiments, an Override switch is implemented in the SafeCT-29 device (see, for example, FIGS. 7A and 8). The Override switch is configured to ensure that the CT scanner can be used (i.e. scans can be performed) in case of a SafeCT-29 failure. It is connected in parallel to the Controlled Interlock Switch. According to some embodiments, the Override Switch is a manually activated switch that is located in close proximity to the CT Operator. When activated, the Controlled Interlock Switch is bypassed and the scanner can be operated regularly.

According to some embodiments, the checker software system is intended for installation in a specified computer. According to some embodiments, the SafeCT-29 Software supports a variety of user interface and functionality features. According to some embodiments, the user operates the software via a standard (small footprint) keyboard, mouse, and the SafeCT-29 Display. According to some embodiments, the SafeCT-29 software includes a configuration file, in which commercial scanners and their software versions are defined, together with the related information on the location of the relevant information on the CT display and the scanner's workflow. The configuration file is continuously updated so that it includes the relevant data of any newly introduced CT scanner model.

According to some embodiments, notifications and permission requests may be provided.

Example 3. Identifying CT Protocols and Dose Data

SafeCT-29 may include one or more configuration files, each includes information about which the location of the relevant information (e.g., radiation dose) on the CT system, such as the CT Display. Such file may also include information on the scanner's workflow. Relevant information may include dose data among other data. Information related to location may refer to position of the relevant information within the CT system, and/or within an image that the CT system produces.

Extracting dose data may be performed on an image, as follows: a video stream is received from the Video Grabber and analyzed continuously in real time. The CT Protocol, the estimated dose levels and exam ID (as appear on the CT display) are extracted.

According to some embodiments, identifying CT Protocol and dose data is performed by OTS OCR software, integrated with the SafeCT-29 Software. The integrated OCR software may preferably meet the following requirements:
  a. may perform OCR reading in a time resolution which is sufficient for making a decision, to ensure that a scan cannot be initiated by the CT operator if the dose values exceed the Notification/Alert values;
  b. may analyzes the picture repeatedly: data items are identified when the OCR output values are consistent, i.e. same results are received, consecutively, for multiple times;
  c. may be capable to identify a protocol name in case of a difference of up to several characters (one or more) between the OCR output and a pre-defined list of protocols;
  d. in the event that the SafeCT-29 software cannot identify a protocol, where the software includes a file of notifications and alerts, the software will search for a name of a group (e.g. "Head") and, if found, will allocate the related notification and alert values; and
  e. OCR accuracy: 99% for numeric values; 85% for text (OCR only). Accuracy of OCR and SafeCT-29 software, as defined in (b)-(e) above: for dose values (numeric data): 99.9% For Protocol data (alphanumeric): 98%.

Example 4. Assessing Dose Level Relative to Thresholds

According to some embodiment, the system continuously compares the estimated dose levels and the protocol data that are extracted from the CT files or from the CT display video, using the OCR, to pre-defined Notification and Alert Values. In case the estimated dose exceeds the Notification Value or the Alert Value, the system performs the following actions:
  a. A notification to the user is displayed on the SafeCT-29 Display
  b. A command is generated to open the Interlock Switch (thus preventing the scan)

In case the system cannot match the Protocol or Protocol name with those defined in the Computer's internal database (for example, if a notification value was not set for the selected CT Protocol), a warning message is displayed to the user on the SafeCT-29 Display.

Example 5. Notifications Display

Notifications, preferably directed to the CT operator, may be displayed on the SafeCT-29 Display (monitor). The SafeCT-29 software may generates the following notifications: Dose data, as extracted from the CT display by the OCR; Dose Notification, in case the estimated dose level is higher than the established Notification value, in accordance with the XR-25 Standard (FIG. 12); Dose Alert, in case the estimated accumulated dose level is higher than the established Alert value in accordance with the) XR-25 Standard (FIG. 13); System status, failures and warnings; and the system is not required to display an alert if a corresponding Alert Value has not been set

Example 6. System Operation Under Notifications and Notifications Removal

According to some embodiments, Dose Notification and Dose Alert may be removed under one or more of the following conditions: (1) the CT Operator changes the protocol's parameters so the estimated dose level does not exceed anymore the notification/alert value; (2) the CT Operator is identified and confirms the selected protocol's parameters. According to some embodiments, the CT Operator may further provide to the system reasoning for the selected protocol's parameters.

The software may generate an audio alert aimed to ensure that the user is aware of a notification, alert or warning that is displayed on the SafeCT-29 display. The audio alert may include at least one tone ("beep") over a span of a few seconds (e.g. 2-6 seconds). The beep tone(s) may be generated by the computer internal speaker. The beep tone may be generated upon one or more of the following conditions: (i) when a Dose Notification or Dose Alert is displayed; and/or (ii) when the software identifies an error or failure that prevents scanning (e.g. Control Interlock Switch failure).

According to some embodiments, scanning is prevented by the system, upon display of a Notification or an Alert. Initially, upon startup, the software closes the Door switch loop. However, when an Alert is displayed on the SafeCT-29 display, the SafeCT-29 Computer may generate a signal that opens the Interlock switch, thus opening the door switch loop and preventing the initiation of a new scan. It should be noted however that neither Dose Notification nor Dose Alert interrupts a scan while in progress.

Thus, in normal operation, the checker-device maintains the CT door switch loop closed (i.e. enabling scanning). Checker-device opens the CT door switch loop when the estimated dose exceeds the pre-defined threshold(s).

Moreover, the checker-device software identifies that the scanner is in "Scan" mode (based on the information that is displayed on the CT Operator Display) and does not allow entering into "Alert Mode" or "Notification Mode" thus preventing potential accidental interruption.

Additionally, the checker-device Interlock Control includes an Interlock Override switch, which maintains the door switch closed during the scan, thus preventing any interruption by the checker-device system during a scan, even in case of a software error or failure.

The SafeCT-29 Display may have one or more of the following modes:
a. Normal operation, in which the identified CT Protocol (or Protocol Element) and the related dose levels are presented on the Display. No user action is required or associated with this mode.
b. Notification: a Dose Notification is displayed on the Display, requiring the user to validate CT dose data and reconfirm the CT Protocol parameters. The Notification disappears (and the display goes back to Normal Operation mode) when the dose levels are set below the Notification Value(s) or when the user confirm the scan parameters
c. Alert: a Dose Alert is displayed on the Display, requiring the user to validate CT dose data and reconfirm the CT Protocol parameters. The Dose Alert disappears (and the display goes back to Normal Operation mode) when the dose levels are set below the Alert Value(s) or when the user confirm the scan parameters
d. Failure: in case of a SafeCT-29, failure information is displayed on the Display. The user shall refer to the User Guide for assistance.

In case of a system failure, the user may disconnect the SafeCT-29 entirely by operating an Override Switch, and continue working with the CT scanning as if SafeCT-29 is not associated with the scanner. The Override Switch status may be displayed to the user.

The SafeCT-29 system may be designed to be "always on." The system automatically enters its operational mode upon power up (no need for any user intervention such as login). The system may be powered-off or restarted through a software command or by powering off the SafeCT-29 PC.

Additionally, while the CT is in operation, the SafeCT-29 display continuously displays any relevant information (i.e. not in "sleep" mode).

The invention claimed is:
1. A Computed Tomography (CT) checker device, comprising:
   an input port configured to be associated with an existing CT-system, the input port configured to obtain scanning data and provide corresponding signal;
   processing circuitry, configured to:
      obtain the scanning data from the input port;
      detect a radiation parameter value from the scanning data;
      compare the detected radiation parameter value with a predetermined threshold; and
      generate an operation-signal based on the comparison, and
   a control unit, connected to a control switch within the CT system, the control unit configured to affect an operation of the CT system, based on the operation-signal, by toggling the state of the control switch thereby preventing radiation,
   wherein the checker is separate from the existing CT system.
2. The device of claim 1, wherein the input port is configured to be associated with a display interface in the CT-system, wherein the scanning data is display imagery and wherein the signal is an internal-display signal, such that, the processing circuitry is configured to:
   obtain the internal-display-signal from the input port;
   analyze imagery depicted by the internal-display-signal;
   detect the radiation parameter value from the analyzed imagery;
   compare the detected radiation parameter value with a predetermined threshold; and
   generate the operation-signal configured to affect an operation of the CT system, based on said comparison, by toggling the state of a CT control switch thereby preventing radiation.

3. The device of claim 2, further comprising a monitor, and said processing circuitry is further configured to provide a display signal to said monitor to indicate a state of operation of the device.

4. The device of claim 3, wherein the state of operation of the device includes a result of the comparison between the detected radiation parameter value and the predetermined threshold.

5. The device of claim 3, wherein said processing circuitry is configured to provide a warning imagery to said display based on the comparison between the detected radiation parameter value and the predetermined threshold.

6. The device of claim 2, further comprising an output port configured to provide a display imagery signal to a monitor in the CT system, wherein the device is configured to be connected on the display link of the CT system and either pass an uninterrupted imagery from the input port to the output port, or provide an interrupted imagery from the input port to the output port based on the comparison between the detected radiation parameter value and the predetermined threshold.

7. The device of claim 2, wherein detecting the radiation parameter value from the analyzed imagery comprises performing an optical character recognition on the analyzed imagery.

8. The device of claim 1, wherein said preventing radiation comprises preventing an initiation of scanning a new scan.

9. The device of claim 1, wherein said CT System comprises a door switch loop and wherein said control switch is connected to the door switch loop.

10. The device of claim 1, further comprising an interface configured to obtain control-input from a user and affect the operation of the device accordingly.

11. A method for CT dose optimization and management, the method comprising:
 providing a CT checker device as claimed in claim 1;
 providing a CT system separate from the CT checker device;
 connecting the control unit of the CT checker device to a control switch within the CT system;
 providing a predetermined threshold value;
 obtaining an internal signal from the CT system, through the input port of the CT checker;
 detecting a radiation parameter value from the internal signal;
 comparing the detected radiation parameter value with the predetermined threshold; and
 toggling the state of the control switch when the radiation parameter value is above the predetermined threshold thereby preventing radiation.

12. The method of claim 11, wherein said CT checker device is associated with a display interface in the CT-system, and said internal signal is an internal-display-signal.

* * * * *

UNITED STATES PATENT AND TRADEMARK OFFICE
CERTIFICATE OF CORRECTION

PATENT NO. : 9,693,747 B2
APPLICATION NO. : 15/209083
DATED : July 4, 2017
INVENTOR(S) : Dan Laor et al.

Page 1 of 1

It is certified that error appears in the above-identified patent and that said Letters Patent is hereby corrected as shown below:

On the Title Page

Item (72) Inventors should read:
(72) Inventors: Dan Laor, Haifa (IL);
 Eliran Dahan, Haifa (IL);
 Eyal Aharon, Kiryat Tivon (IL);
 Shai Attia, Shimshit (IL)

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*